United States Patent [19]
Federighi et al.

[11] Patent Number: 5,773,300
[45] Date of Patent: Jun. 30, 1998

[54] NEOPLASIA DIAGNOSTIC METHOD

[75] Inventors: David A. Federighi, Kirkland; Stuart L. Bursten, Snoqualmie, both of Wash.

[73] Assignee: Cell Therapeutics, Inc., Seattle, Wash.

[21] Appl. No.: 842,150

[22] Filed: Apr. 23, 1997

Related U.S. Application Data

[63] Continuation of Ser. No. 443,655, May 18, 1995, abandoned.

[51] Int. Cl.$^6$ .................................................. G01N 33/50
[52] U.S. Cl. .............................. 436/64; 436/71; 436/129; 436/813
[58] Field of Search ............................. 436/64, 71, 129, 436/161, 175, 813, 815

[56] References Cited

U.S. PATENT DOCUMENTS

| | | | |
|---|---|---|---|
| 5,075,101 | 12/1991 | Siguel | 424/9 |
| 5,362,649 | 11/1994 | Schwertner | 436/71 |
| 5,470,714 | 11/1995 | Kleinfeld | 435/7.8 |
| 5,508,307 | 4/1996 | Horrobin et al. | 514/560 |

OTHER PUBLICATIONS

Begin, M.E. "Differential Killing of Human Carcinoma Cells Supplemented with n–3 and n–6 Polyunsaturated Fatty Acids" Journal of the National Cancer Institute, vol. 77, No. 5 (1986) pp. 1053–1059, Nov. 1986.

Chaudry, A. et al. "Essential Fatty Acid Distribution in the Plasma and Tissue Phospholipids of Patients with Benign and Malignant Prostatic Disease" British Journal of Cancer, vol. 64 (1991) pp. 1157–1160.

Bursten, S.L. et al. "An Increase in Serum C18 Unsaturated Free Fatty Acids as a Predictor of the Development of Acute Respiratory Distress Syndrome" Critical Care Medicine, vol. 24, No. 7, (1996) pp. 1129–1136.

Allain et al., Clin. Chem., vol. 20, No. 4, pp. 470–475 (1974), "Enzymatic Determination of Total Serum Cholesterol".

Ambika Devi et al., Birkhauser Verlag Basel, vol. 50, pp. 489–492 (1994), "Antiproliferative Effect of Polyunsaturated Fatty Acids and Interleukin–2 on Normal and Abnormal Human Lymphocytes".

Bougnoux et al., Br. J. Cancer, vol. 70, pp. 330–334 (1994), "α–Linolenic Acid Content of Adipose Breast Tissue: A Host Determinant of the Risk of Early Metastasis in Breast Cancer".

U.N. Das, Nutrition, vol. 6, No. 6, pp. 429–434 (1990), "Gamma–Linolenic Acid, Arachidonic Acid, and Eicosapentaenoic Acid as Potential Anticancer Drugs".

du Toit et al., Prostaglandins Leukotrienes and Essential Fatty Acids, vol. 51, pp. 121–124 (1994), "The Effect of Gamma–Linolenic Acid and Eicosapentaenoic Acid on Urokinase Activity".

Falconer et al., Br. J. Cancer, vol. 69, pp. 826–832 (1994), "Effect of Eicosapentaenoic Acid and Other Fatty Acids on the Growth in Vitro of Human Pancreatic Cancer Cell Lines".

Grammatikos et al., Br. J. Cancer, vol. 70, pp. 219–227 (1994), n–3 and n–6 Fatty Acid Processing and Growth Effects in Neoplastic and Non–Cancerous Human Mammary Epithelial Cell Lines.

Hyman et al., Journal of Neurochemistry, vol. 37, pp. 60–69 (1981), "Accumulation of N–3 Polyunsaturated Fatty Acids by Cultured Human Y79 Retinoblastoma Cells".

Mengeaud et al., Prostaglandins Leukotrienes and Essential Fatty Acids, vol. 47, pp. 313–319 (1992), "Effects of Eicosapentaenoic Acid, Gamma–Linolenic Acid and Prostaglandin $E_1$ on Three Human Colon Carcinoma Cell Lines".

Sangeetha Sagar et al., Cancer Letters, vol. 63, pp. 189–198 (1992), "Cytotoxic Action of cis–unsaturated Fatty Acids on Human Cervical Carcinoma (HeLa) Cells: Relationship to Free Radicals and Lipid Peroxidation and its Modulation by Calmodulin Antagonists".

Yoshioka et al., Journal of Lipid Research, vol. 26, pp. 1134–1141 (1985), "Phospholipid (diacyl, alkylacyl, alkenylacyl) and Fatty Acyl Chain Composition in Murine Mastocytoma Cells".

Primary Examiner—Jeffrey Snay
Attorney, Agent, or Firm—Stephen Faciszewski; Cynthia L. Shumate

[57] ABSTRACT

There is disclosed a diagnostic assay for determining the presence of a neoplasia or a tumor burden in a mammal comprising (a) measuring the amount of unsaturated free fatty acids (FFAs) linolenate and arachidonate in a body fluid, and (b) determining a ratio value comprising the sum of linolenate and the sum of arachidonate.

7 Claims, 6 Drawing Sheets

Bayesian Analysis of Combined Human Data

Discriminator tested: 0.7

|  |  | Disease | | Total |
|---|---|---|---|---|
|  |  | + | - |  |
| Test | + | 28 | 2 | 30 |
| .07 | - | 9 | 13 | 22 |
|  |  | 37 | 15 | 52 |

| | | |
|---|---|---|
| Sensitivity = | 28/37 = | 0.76 |
| Specificity = | 13/15 = | 0.87 |
| Accuracy, + = | 28/30 = | 0.93 |
| Accuracy, - = | 13/20 = | 0.60 |
| Likelihood = | 5.84 | |

5,773,300

NEOPLASIA DIAGNOSTIC METHOD

This is a continuation of U.S. application Ser. No. 08/443,655 filed May 18, 1995, now abandoned.

TECHNICAL FIELD OF THE INVENTION

The present invention provides a diagnostic assay for the presence of neoplasia or a tumor burden in a mammal. The successful method was achieved by examining the proportionality of the distribution of major free fatty acids (FFAs) present in serum of diseased and normal humans and in diseased and normal animal models.

BACKGROUND OF THE INVENTION

Cancer diagnosis has always been a difficult procedure. There have been many ways of diagnosing cancer, that usually involve specific types of cancers when taking chemical measurements or by localizing tumors using various imaging techniques (X-rays, MRI, palpitation, biopsy, etc.). Many tumor diagnostic procedures uses localizing agents that bind to tumor-specific antigens, but these are specific to certain types of tumors. What is needed is a chemical procedure that can detect neoplasia or cancer of any type that is not specific to any particular kind of cancer. This present invention addresses this need in the art.

The free fatty acids (FFAs) linoleate and linolenate are essential fatty acids (EFAs) and can not be synthesized by mammals. EFAs must be obtained through diet. Once provided, EFAs can be elongated, desaturated, and retroconverted by normal mammalian cells to produce polyunsaturated fatty acids. The FFAs γ-linolenate and arachidonate are derived from linoleate.

Polyunsaturated FFAs accumulate in the cellular membrane of cancer cells affecting its fluidity (Yoshioka et al., *J. Lipid Res.* 26:1134–1141, 1985; Hyman and Spector, *J. Neurochemistry* 37:60–69; 1981; and Mengeuard et al., *Prostaglandin's Leukotrienes Essential Fatty Acids* 47:313–319, 1992). Grammatikos et al. (*Annals NY Acad. Sci.* 745:95–105, 1994 and *Br. J. Cancer* 70:219–227, 1994) suggested that tumor cells cannot desaturate FFAS.

Adding γ-linolenate to tumor cells in culture has shown a decrease in urokinase, an important enzyme in carcinogenesis and tumor metastasis (du Toit et al., *Prostaglandin's Leukotrienes Essential Fatty Acids* 51:121–124, 1994). γ-Linolenate elevates production of lipid peroxides and superoxides (Devi and Das, *Experientia* 50:489–492, 1994; Falconer et al., *Br. J. Cancer* 69:826–832, 1994; Sagar et al., *Cancer Lett.* 63:189≧198, 1992; and Das, *Nutrition* 6:1157–1160; 1990). A low level of α-linolenate in adipose breast tissue shows an increased risk of metastasis in breast cancer (Bougnoux et al., *Br. J. Cancer* 70:330–334, 1994). Analysis of the free fatty acid composition of prostate cancer cells versus normal prostate cells showed a decrease in arachidonate (Chaudry et al., *Br. J. Cancer* 64:1157–1160, 1991). Therefore, there is no disclosure or suggestion in the art to measure lipids or FFAs to diagnose the presence of neoplasia or cancer.

SUMMARY OF THE INVENTION

The present invention provides a diagnostic assay for determining the presence of neoplasia or a tumor burden in a mammal, comprising (a) measuring the amount of free fatty acids (FFAs) linoleate and arachidonates in a body fluid, and (b) determining a ratio value comprising the sum of the linolenate and the sum of the arachidonate. Preferably, the ratio value comprises the sum of linolenate, divided by the sum of arachidonate or the sum of arachidonate divided by the sum of linolenate.

Preferably, the body fluid is plasma or a plasma-sourced body fluid (e.g., urine, sweat, saliva or tears). There are several means for measuring the amount of linolenate and arachidonate. These include, for example, HPLC (high performance liquid chromatography), GC (gas chromatography), TLC (thin layer chromatography), and immunoassays using antibodies specific for the specific FFAs.

DETAILED DESCRIPTION OF THE INVENTION

The present invention provides a diagnostic assay for determining the presence of a neoplasia or a tumor burden in a mammal comprising (a) measuring the amount of unsaturated free fatty acids (FFAs) linolenate and arachidonate in a body fluid, and (b) determining a ratio value comprising the sum of linolenate and the sum of arachidonate. Preferably, the linolenate FFA is the sum of the alpha, gamma and omega linolenate FFAs. Preferably, the ratio value comprises the sum of linolenate divided by arachidonate, or the ratio value comprises the sum of arachidonate divided by the sum of linolenate. Preferably, the body fluid is plasma or a plasma-sourced body fluid, and most preferably, the plasma or plasma-sourced body fluid has neutral lipids removed before the assay procedure. Preferably, the means for measuring the amount of arachidonate and linolenate is selected from the group consisting of HPLC (high performance liquid chromatography), GC (gas chromatography), TLC (thin layer chromatography), immunoassays using antibodies specific for the specific FFAs, and combinations thereof.

Changes in serum levels of these FFAs can be used as a diagnostic indicator of cancer, to monitor the progression of the disease, and to evaluate the efficacy of therapy. To do so it is necessary to quantitatively separate these FFAs from the other lipids found in serum. A preferred means is a combination of chemical extraction and chromatography.

The serum free fatty acid levels from mice with a variety of advanced tumors were compared to the free fatty acid levels of control mice. It was observed that the acyl ratio, linolenic acid divided by arachidonic acid, was higher in serum from mice with tumors than in control mice. Having established a relationship between the acyl ratio and advanced tumors, the relationship between acyl ratio and tumor volume was investigated. Mice were inoculated subcutaneously with 3LL β-galactosidase cells and were sacrificed at various stages of tumor development. Their serum free fatty acids were analyzed. An increase in the ratio of linolenic acid divided by arachidonic acid was observed as the volume of tumors increased. However, as tumors grew to a very large volume, the ratio fell. This was possibly due to necrosis of the tumor's interior.

Serum samples of human cancer patients were obtained from the Webb-Waring Institute, Denver, Colo. Analysis of serum free fatty acids were run in a blinded manner. When the code was broken, cancer patients showed an elevated ratio of linolenic acid divided by the arachidonic acid compared to the ratios of normal subjects.

The high performance liquid chromatograph (HPLC) used was a computer controlled model 517 from Gilson Medical Electronics, Inc. (Middleton, Wis.). The HPLC consisted of two 306 high pressure pumps, a 805 manometric module, a 811C dynamic mixer, a 231 sample injector, a 401 dilutor, 506C interface, and a 121 Fluorometer. Additionally, a Linear UVIS 200 ultra violet detector (Linear Instruments Reno, Nev.) was used. For serum lipid separation, a 4.6 mm×25 cm silica 80-125-C5 column from Rainin Instrument Co. Inc. (Emeryville, Calif.) was used.

For free fatty acid (FFA) separation, a 4.6 mm×15 cm, 3 micron, Spherisorb ODS2 column was connected in tandem with a 4.6 mm×25 cm, 5 micron, Spherisorb C8 column (Alltech Associates, Inc., Deerfield, Ill.). Acetonitrile, methanol, hexane, isopropanol, chloroform, ethyl acetate, acetone, and water were all HPLC grade from Baxter (Muskegon, Mich.). Potassium chloride, quinuclidine, 9-anthraldehyde, N-chlorosuccinimide, hydrozine monohydrate, used in lipid extraction, and FFA derivitization were obtained from Aldrich (Milwaukee, Wis.). GF/F sintered glass filters were from Whatman International, Ltd., Maidstone, England. Murine blood samples were drawn in heparinized tubes, the serum was separated by centrifugation, then stored at −70° C. until analyzed. Blood samples from human cancer patients were drawn at the Webb-Waring Institute, Denver, Colo. The samples were shipped on dry ice for analysis. The analyses of the human samples were performed in a blinded manner.

Serum FFA analysis was performed in five steps: lipid isolation from the serum matrix by organic extraction; separation of FFAs from the other lipid classes by HPLC; derivatization of the FFA fraction to facilitate fluorescence detection; FFA separation by reverse HPLC; and quantitation by comparison to derivatives of FFA standards. The organic extraction was by the method of Folch et al. It was modified to accommodate the small sample size. Specifically, a 1.0 mg/mL solution of heptadecanoic acid in methanol was made as the internal standard. 12.5 μL internal standard was added to a 15 mL conical glass centrifuge tube then evaporated to dryness under a stream of $N_2$. 350 μL of the serum sample was added followed by 5.0 mL chloroform:methanol (2:1). The sample was vigorously vortex mixed for 2.0 minutes then filtered through a sintered glass filter into a clean 15 mL conical glass centrifuge tube. 1.0 mL of 0.1N KCl was added, the sample vigorously vortex mixed for 2.0 minutes, and phases allowed to separate. The upper phase was removed and the lower chloroform phase, containing the extracted lipids, was dried under a stream of $N_2$.

The choice of a means for measuring FFAs can be any means to measure and distinguish FFAs (preferably multiple unsaturated FFAs) in the $C_{14}$–$C_{22}$ range and distinguish saturated from unsaturated FFAs. Preferred means include TLC (thin layer chromatography), reverse phase HPLC, GC and immunoassays. It is also preferable to first conjugate the FFAs to a conjugation molecule to better detect and distinguish FFAs.

Chemical extraction can be accomplished, for example, by the method of Bligh et al. (*Canadian J. Biochem. Physiol.* 37:914–917, 1959) or that of Folch et al. (*J. Biochem.* 226:497–509, 1957). Briefly, the method of Bligh et al. involves an organic extraction of lipids from biological tissue homogenates or fluids. One volume of sample and three volumes of methanol:chloroform (2:1) were vigorously shaken for 2 min. One volume of chloroform was added and then shaken vigorously for 30 sec. One volume of water was added and then shaken vigorously for 30 sec. The mixture was filtered and the upper aqueous layer was discarded. The lower organic layer contained a mixture of lipid classes, including FFAs. The method of Folch et al. involves the extraction of lipids from biological tissue homogenates or body fluids. One volume of sample plus 20 volumes of chloroform:methanol (2:1) were vigorously shaken for 2 min. The mixture was filtered and an amount of 0.1N KCl equal to 20% of the extraction mixture volume was added and the mixture was shaken vigorously for 2 min. The aqueous and organic phases were allowed to separate. The upper aqueous layer was discarded. The lower organic layer contained a mixture of lipid classes, including FFAs. Free fatty acids and neutral lipids were separated from phospholipids by normal phase high performance liquid chromatography (HPLC) by modifying the method of Van Kessel et al. (*Biochim et Biophys Acta* 486:524–530, 1977). This method involves separation of lipids into their major classes by normal phase (silica) high performance liquid chromatography (HPLC). A 5 micron, 25 cm×0.45 cm silica HPLC column was connected to a binary solvent delivery system followed with a UV detector. The lipid sample was injected on the column and a solvent gradient was run at 1.0 ml/min. The solvent gradient was hexane:isopropanol:water in the proportions 3:4:0.075 run isocratically for 3 min, then ramped to hexane:isopropanol:water in the proportions 3:4:0.75 in 15 min, then run isocratically at the same proportions for 15 min. Detection was at 206 nm. The FFAs and neutral lipids eluted in the first 5 min.

Gas-liquid chromatography (GLC) with flame ionization or mass detection is a preferred method for FFA analysis (Christie, *High-performance Liquid Chromatography and Lipids.* Pergamon Press 1987). This method used an open fused silica columns to separate derivatized FFAs at a relatively low cost with high sensitivity and good quantitation, but the high injection temperatures (e.g., 190° C.) involved risks thermal degradation of the unsaturated FFAs before detection. Methods using reverse phase HPLC with Ultraviolet (UV) or fluorescent detection are most preferred. Published methods have coelution problems especially with oleic acid (C18:1) and palmitic acid (C16:0). We have developed a preferred HPLC method to separate and quantitate the FFAs of interest. The preferred method is described in examples 1 and 2.

EXAMPLE 1

Figure 1:
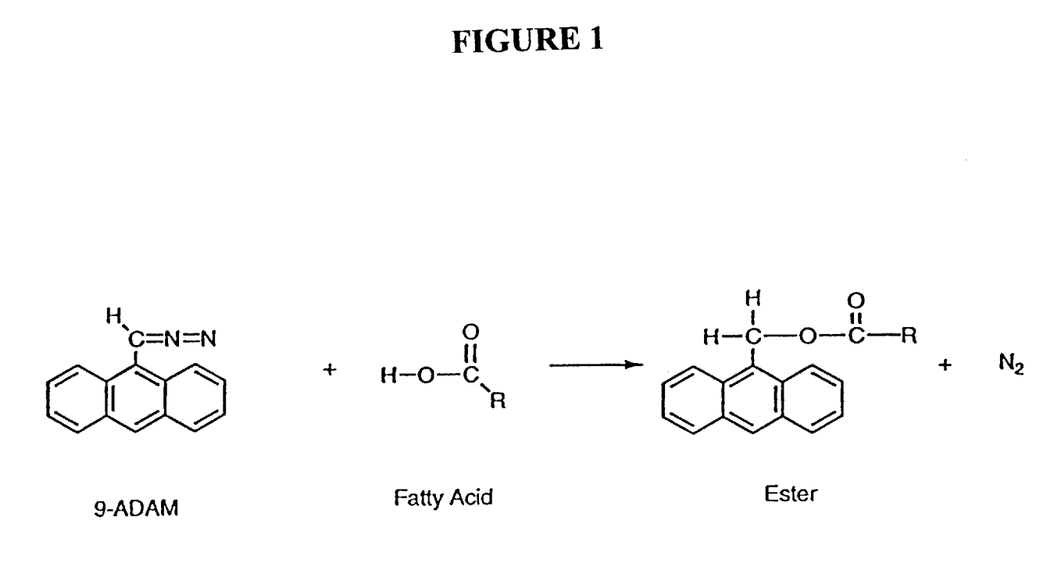
FIG. 1 illustrates the chemistry of a reaction to derivatize FFAs with 9-ADAM.

This example illustrates a preparation of anthroyl fatty acid derivatives. Fatty acid derivatives of 9-anthroyl diazomethane (9-ADAM), which absorbs light at 254 nm and fluoresces with emission at 410 nm, were prepared essentially according to the method described in Nakaya et al. (*Bull. Chem. Soc. Japan* 40:691–692, 1967) and Yoshida et al. (*Analytical Biochem.* 173:70–74, 1988). The derivatization is based on the reaction shown in FIG. 1. Briefly, 9-anthraldehyde hydrazone for 9-anthroyl diazomethane derivafization was synthesized from 9-anthraldehyde and hydrazine monohydrate as follows: (a) 8.8 g 9-anthraldehyde (Aldrich Milwaukee, Wis.) was dissolved in 150 mL absolute ethanol and 8 mL hydrazine monohydrate (Aldrich Milwaukee, Wis.) was added dropwise with continual stirring. (b) The mixture cleared as hydrazine was added then turned opaque as the last drops were added. (c) The reaction was stirred at room temperature for 3 hr, then was filtered (Whatman #1 filter paper, Whatman Int. Maidstone UK) and dried. (d) The product was recrystalized twice with absolute ethanol. (e) The yield was 3.1 g of needle-like crystals.

Figure 2:
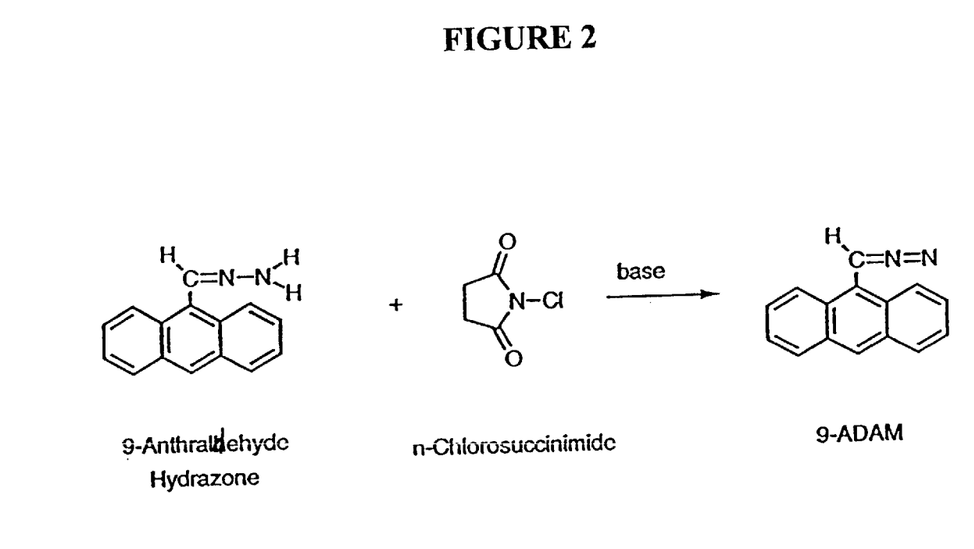
FIG. 2 illustrates the chemistry of a reaction to make a 9-ADAM derivatizing reagent.

The following solutions were made in ethyl acetate: 9-anthraldehyde hydrazone (0.0276M, 0.0304 g/5 mL), Quinuclidine (0.2760M, 0.1534 g/5 mL (oxidizing reagent)), and N-chlorosuccinimide (0.0276M, 0.0184 g/5 mL (catalyst)). Equal volumes of these solutions were mixed to react at room temperature for 30 min. The resulting 9-anthryl diazomethane (9-ADAM) was unstable and was made fresh daily. This reaction is shown in FIG. 2.

The derivatization reaction was carried out by diluting 50 μL of each FFA standard to 200 μL with methanol. FFA standards (1.0 mg/mL) were made up in methanol using: Heptadecanoic acid 17:0 (Aldrich Chemical Milwaukee, Wis.); Arachidonic acid 20:4 (Matreya, Inc., Pleasant Gap, Pa.); Linoleic acid 18:2 (Matreya, Inc., Pleasant Gap, Pa.); Linolenic acid 18:3 (Matreya, Inc., Pleasant Gap, Pa.); Palmitic acid 16:0 (Matreya, Inc., Pleasant Gap, Pa.); Oleic acid 18:1 (Matreya, Inc., Pleasant Gap, Pa.); Stearic acid 18:0 (Matreya, Inc., Pleasant Gap, Pa.); Myristic acid 14:0 (Matreya, Inc., Pleasant Gap, Pa.); Lauric acid 12:0 (Matreya, Inc., Pleasant Gap, Pa.); Arachidic acid 20:0 (Matreya, Inc., Pleasant Gap, Pa.); and n-Docosanoic acid 22:0 (Matreya, Inc., Pleasant Gap, Pa.). Additionally, the following standards were dissolved in methanol (50 μg/mL): 5-HETE 20:4; 12-HETE 20:4; and 13-HODE 18:2 (Biomol Research Laboratories, Inc., Plymouth Meeting, Pa.). Derivatizing solution (200 μL) was added. The mixture was reacted for 1 hr at room temperature to form each derivatized standard. 20 μL was injected into an HPLC and run by a reverse phase method described below.

EXAMPLE 2

This example illustrates the reverse phase HPLC procedure used to separate and quantitate the derivatized anthroyl FFAs. A reverse phase "C8" column (4.6 cm×25 cm, 5 micron Spherisorb® C8, Alltech Associates, Inc. Deerfield, Ill.) separated the saturated FFAs, and a reverse phase "C18" column (4.6 mm×15 cm, 3 micron Spherisorb® ODS2 Alltech Associates, Inc. Deerfield, Ill.) separated the unsaturated FFAs. Neither column individually could resolve all the derivatized FFA standards. To solve the problem, a 3 micron, 15 cm "C18" column was connected to the HPLC followed by a 5 micron, 25 cm "C8" column. The high performance liquid chromatograph was a model 517 from Gilson Medical Electronics, Inc., Middleton, Wis. Two detectors were connected in tandem. The first was Model UVIS 200 from Linear Instruments, Reno, Nev. The second was Model 121 Fluorometer from Gilson Medical Electronics.

Table 1 below shows the chromatographic conditions used.

TABLE 1

| | |
|---|---|
| UV Detection: | 254 nm |
| Fluorescent Detection: | Excitation: 305–395 nm bandpass filter |
| | Emission: 430–470 nm bandpass filter |
| Buffer A: | 70% Acetonitrile: 30% $H_2O$ |
| Buffer B: | 100% Acetonitrile |
| Flow: | 1.0 mL per min |
| Gradient: | 40% B for 2 min |
| | from 40% to 45% B in 18 min |
| | from 45% to 54% B in 10 min |
| | from 54% to 76% B in 5 min |
| | from 70% to 94% B in 19 min |
| | from 94% to 99% B in 1 min |
| | 99% B for 29 min |
| | from 99% to 40% B in 1 min |
| | 40% B for 5 min |

Using the HPLC system described, we separated individual derivatized FFAs. Levels of detection were in low nanogram quantities. Once separation and quantitation of FFA levels was achieved an animal model was examined in example 3.

EXAMPLE 3

This example illustrates a study of normal and tumor-bearing mice showing that the inventive diagnostic method was able to distinguish tumor load by a simple blood test. Healthy mice (n=5) and mice with subcutaneous 3LL and B16 melanoma tumors of varying sizes (n=15) had serum lipids extracted by a Folch extraction as described above. The free fatty acids were derivatized as described in examples 1 and 2 and then separated using a dual column (C18) reverse phase isocratic gradient. The totals of linolenate and arachidonate were determined using standard curves and the ratio (linolenate/arachidonate) was determined.

Figure 3:
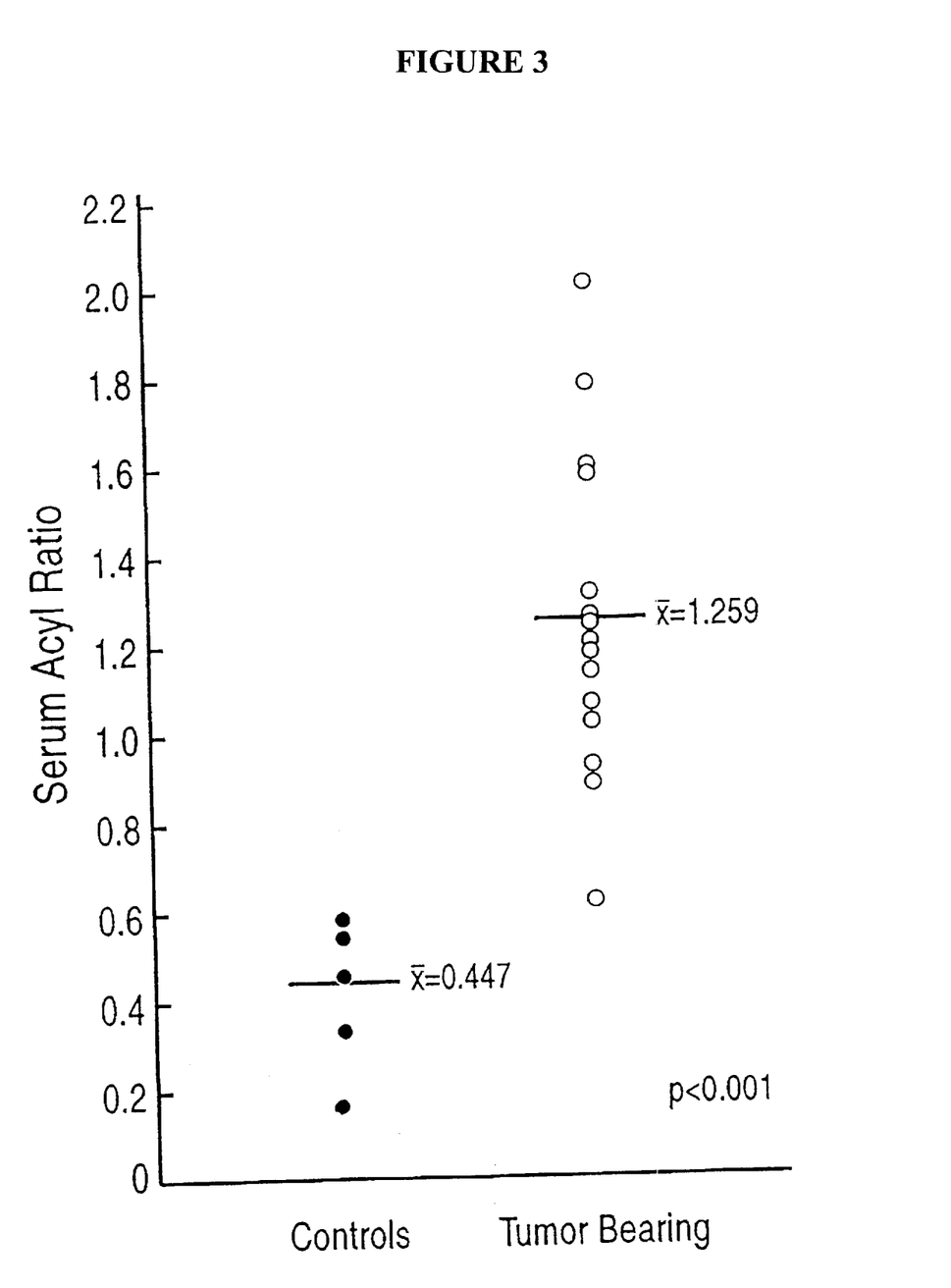
FIG. 3 shows a Bayesian plot of serum FFA ratios (linolenate/arachidonate) of 15 mice with tumors and 5 control mice. The serum was obtained from control animals in ongoing anti-tumor drug in vivo experiments, but the sera used were always from an untreated control group. No segregation of tumor type or size was made. In all cases but one, the serum FFA ratio of the mice with tumors was significantly higher than that of the control mice.

FIG. 3 shows a Bayesian plot of the serum FFA ratios (linolenate/arachidonate) of 15 mice with tumors and 5 control mice. No segregation of tumor type or size was made. In all cases but one the serum FFA ratio of the mice with tumors was higher than that of the control mice.

EXAMPLE 4

This example illustrates an experiment to determine the sensitivity of the assay. Eighteen female BDF1 mice were inoculated with $2\times10^6$ 3LL β-galactoside cells subcutaneously in the right scapular region. A 0.5 cc insulin syringe attached to a 28 gauge needle was used to deliver 0.1 cc of cells. Fifteen of these mice were to be used to study the free fatty acid content of the blood at repeated tumor doubling times. There were five bleeding time points, corresponding to doubling times, with three animals per time point. Three BDF1 mice were not inoculated with cells and were bled as normal controls. The remaining three mice inoculated with $2 \times 10^6$ cells were bled for the above-described FFA assay (labeled as such) when the tumor reached a "medium" size. Three additional BDF1 mice were not inoculated with cells (normal) and three mice were injected with sterile RPMI media. These mice were bled at the same time as the FFA assay mice and served as controls.

The mice inoculated with 3LL B-galactoside cells were measured for tumor volume using digital calipers. This was considered the starting volume, and three mice were bled. The animals were humanely euthanatized by $CO_2$ asphyxiation and bled via cardiocentesis using a 1 cc syringe and 27 gauge needle coated with 10% EDTA. The blood was expelled through a needleless syringe into a clean tube also with EDTA (0.1 ml per 1.0 ml of blood). Samples were spun in a centrifuge (12100 RPM) for 5 minutes and the resulting plasma was pippetted into tubes. Samples were immediately stored in a −70 degree C freezer. The following Table 2 summarizes the experimental design.

TABLE 2

| Animal Number | day 0 Tumor Vol. (mm³) | day 2 Tumor Vol. (mm³) | day 6 Tumor Vol. (mm³) | day 10 Tumor Vol. (mm³) | Day of Bleeding |
|---|---|---|---|---|---|
| 3971 | 166 | | | | 0 |
| 4115 | 128 | | | | 0 |
| 4121 | 222 | | | | 0 |
| 3967 | 203 | 440 | | | 2 |
| 3975 | 169 | 355 | | | 2 |
| 4113 | 94 | 258 | | | 2 |
| 2654 | 96 | 95 | 568 | | 6 |
| 3966 | 208 | 198 | 1161 | | 6 |
| 3969 | 57 | 131 | 670 | | 6 |
| 2666 | 61 | 77 | 565 | 1016 | 10 |
| 2674 | 132 | 224 | 958 | 1779 | 10 |
| 3973 | 31 | 119 | 661 | 2000 | 10 |

Due to rapid growth and ulceration of this tumor line, we were unable to obtain five time points. All animals with tumors of compromising size or gross ulceration, were humanely euthanatized. The animals for each time point were selected based on the previous tumor volume; those mice that nearly doubled since the last measurement were bled as on day 0. Measurements were performed on the second, sixth, and tenth days. Three mice were bled following each measurement (see table above). Three normal control mice (#4120, 4117 and 4118) which received no injection of cells, were bled as on day 0.

Figure 4:
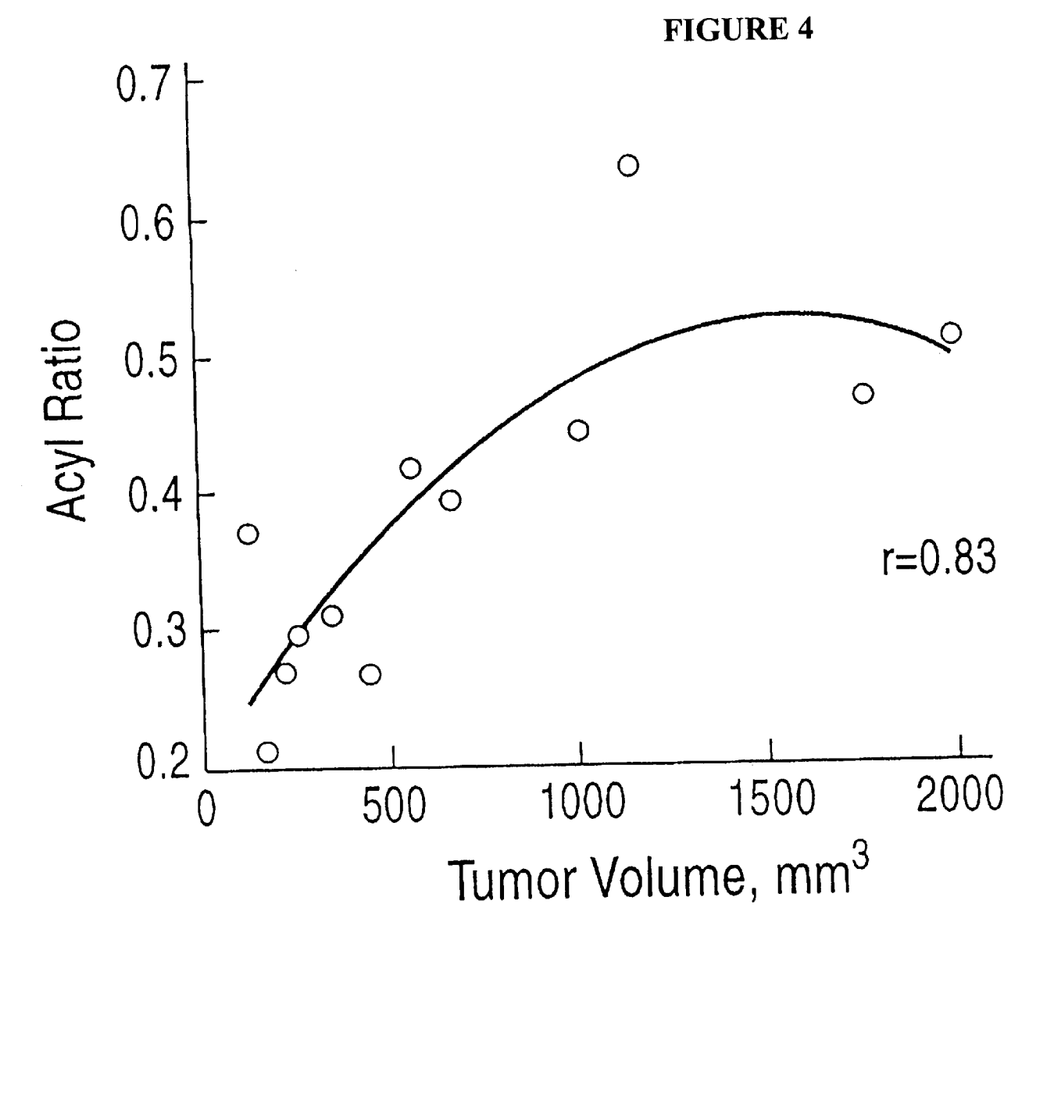
FIG. 4 shows a the relationship of the linolenate/arachidonate FFA ratio plotted against measured tumor volume in female BDF-1 mice inoculated subcutaneously with $2 \times 10^6$ 3LL β-galactosidase cells. These data show the sensitivity of the diagnostic assay to tumor volume.

Female BDF-1 mice were inoculated subcutaneously with $2 \times 10^6$ 3LL β-galactosidase cells and B16 melanoma tumors of measured sizes (by volume in mm³) had serum lipids extracted, separated, derivatized and separated FFAs by the procedure described herein. The serum FFA linolenate and arachidonate sums were determined and the serum FFA (linolenate/arachidonate) ratio determined. The relationship of the linolenate/arachidonate FFA ratio plotted against measured tumor volume in female BDF-1 mice. Five time points were taken, corresponding to tumor volumes of approximately 100, 300, 500, 700 and 1000 mm³. These data show the sensitivity of the diagnostic assay to tumor volume. Acyl ratios (linolenate/arachidonate) demonstrated a polynomial correlation of 0.83 (p<0.05 acyl ratios and tumor volume that were related through two variables) with a variance of 0.69 in acyl ratios due to tumor volume. However, as tumors grew to a very large volume the serum FFA ratio fell. This was possibly due to necrosis of the tumor's interior.

EXAMPLE 5

Figure 5:
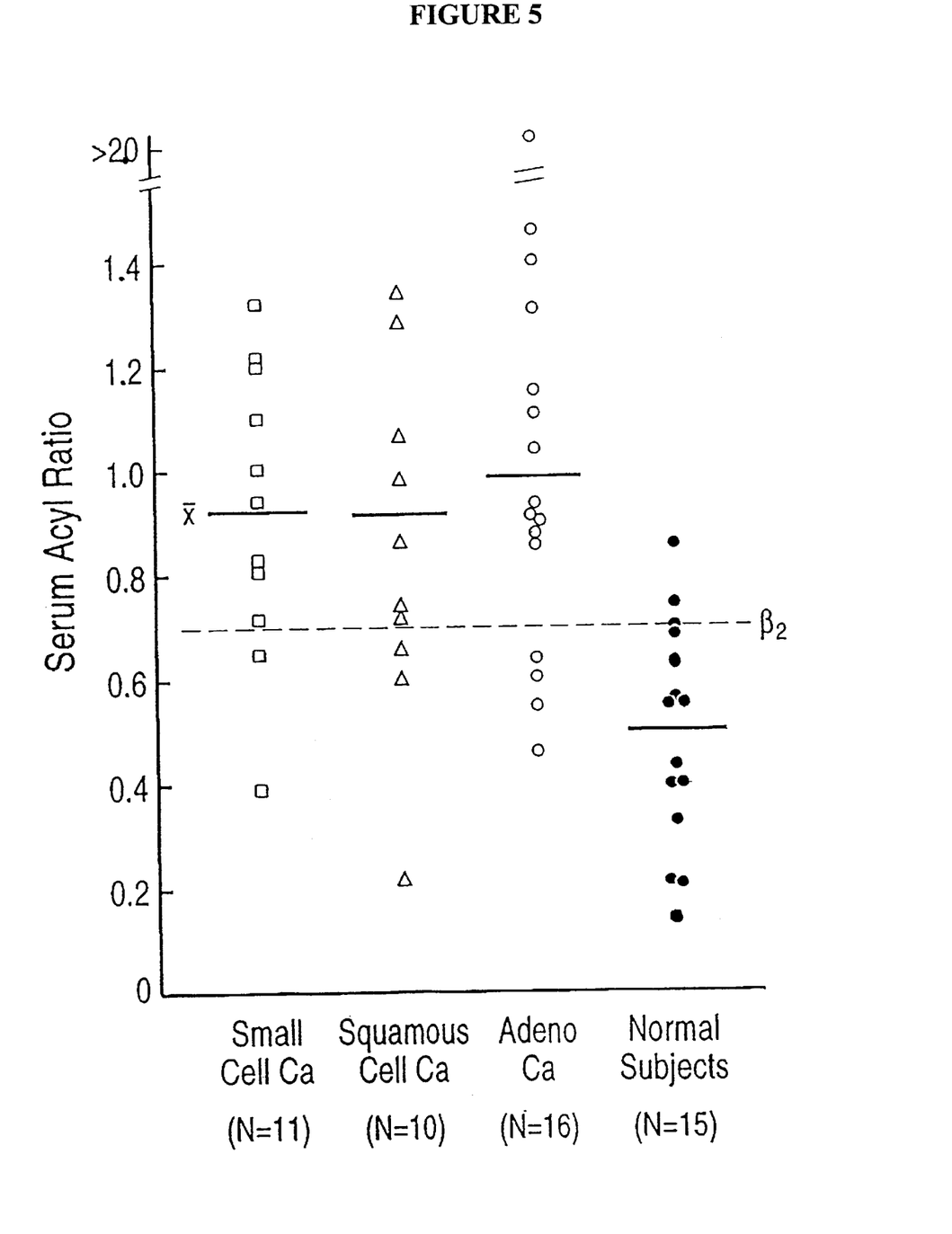
FIG. 5 shows a Bayesian plot of the mean linolenate/arachidonate FFA ratios of cancer patients and normal volunteers. Thirty nine blinded serum samples from human lung cancer patients were received and the diagnostic assay performed as described herein. After completion of the analyses, the code was broken and the samples were divided into three groups according to a confirmed diagnosis of small cell cancer, squamous cell carcinoma and adenocarcinoma.
Figure 6:
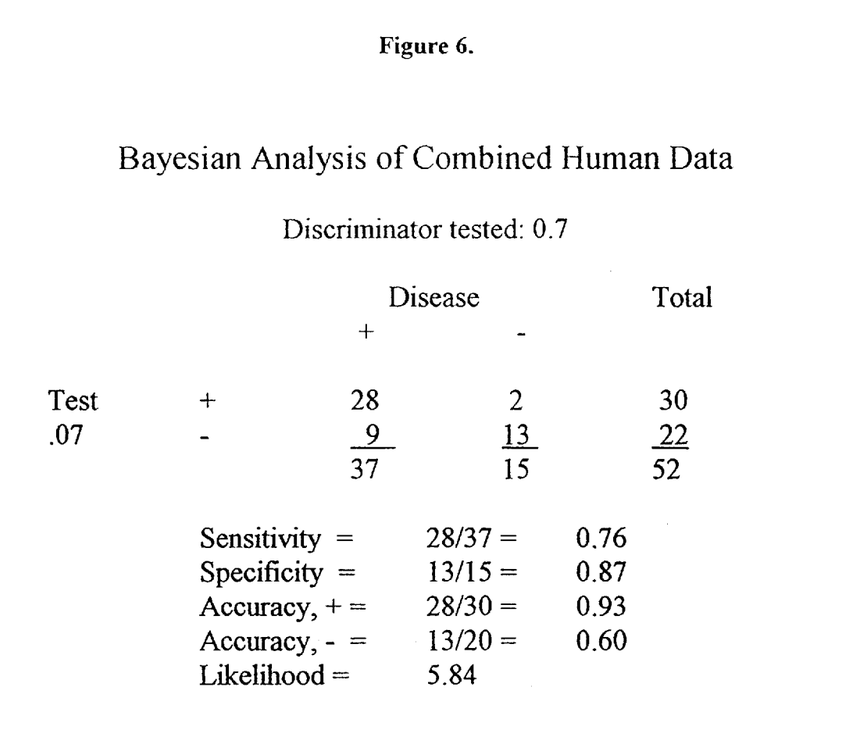
FIG. 6 shows the Bayesian analysis of the combined human data provided in FIG. 5, wherein sensitivity equals 0.76, specificity equals 0.87, positive predictive value equals 0.93, negative predictive value equals 0.60 and likelihood equals 5.8.

This example illustrates an experiment to measure the serum FFA ratios of patients who were diagnosed with varying lung tumors and from healthy control subjects. Human sera were obtained from healthy control subjects (n=15) and patients with varying lung tumors diagnosed by bronchoscopy and biopsy (small cell n=11; squamous cell n=10; and adenocarcinoma n=16). Blinded serum samples from human lung cancer patients were received from the Webb-Waring Institute and the serum FFAs analyzed as outlined. The code was then broken, the samples divided into 3 groups. Those with small cell cancer had acyl ratios with a mean of 0.91, range between 0.38–1.32, and p<0.001. Those with squamous cell carcinoma had acyl ratios with a mean of 0.84, range between 0.21–1.33, and p<0.05. Those with adenocarcinoma had acyl ratios with a mean of 0.98, range between 0.43–2.09 and p<0.001. The results are shown in the Bayesian plot of FIG. 5. It can be seen that the mean values of the acyl ratios of the cancer patients are significantly higher than the mean value of the acyl ratios of the normal group. FIG. 6 shows the Bayesian analysis of the combined human data; sensitivity equals 0.76, specificity equals 0.87, positive predictive value equals 0.93, negative predictive value equals 0.60, and likelihood equals 6.

Measurable differences in the serum fatty acid acyl ratios (linolenate/arachidonate) of patients with tumors versus normal subjects were detected. The difference depends upon tumor volume. The acyl ratios are a useful tool in monitoring the effectiveness of anti-cancer treatments.

We claim:

1. A diagnostic assay for determining the presence of a neoplasia or a tumor burden in a mammal comprising (a) measuring the amount of unsaturated free fatty acids (FFAs) linolenate and arachidonate in a body fluid, (b) determining a ratio value comprising the sum of linolenate and the sum of arachidonate, and (c) determining the presence of a neoplasia or a tumor burden from said ratio volume.

2. The diagnostic assay of claim 1 wherein the linolenate FFA is the sum of the alpha, gamma and omega linolenate FFAs.

3. The diagnostic assay of claim 1 wherein the ratio value comprises the sum of linolenate, divided by arachidonate.

4. The diagnostic assay of claim 1 wherein the ratio value comprises the sum of arachidonate, divided by the sum of linolenate.

5. The diagnostic assay of claim 1 wherein the body fluid is plasma or a plasma-sourced body fluid.

6. The diagnostic assay of claim 5 wherein the plasma or plasma-sourced body fluid has neutral lipids removed before the assay procedure.

7. The diagnostic assay of claim 1 wherein a means for measuring the amount of arachidonate and linolenate is selected from the group consisting of HPLC (high performance liquid chromatography), GC (gas chromatography), TLC (thin layer chromatography), immunoassays using antibodies specific for the specific FFAs, and combinations thereof.

* * * * *